(12) United States Patent
Hoffmann et al.

(10) Patent No.: US 7,700,654 B2
(45) Date of Patent: Apr. 20, 2010

(54) ISOLATION OF N-BUTYLBENZENESULFONAMIDE, SYNTHESIS OF BENZENESULFONAMIDE DERIVATIVES, AND USE OF N-BUTYLBENZENESULFONAMIDE AND BENZENESULFONAMIDE DERIVATIVES FOR TREATING BENIGN PROSTATIC HYPERPLASIA AND/OR PROSTATE CARCINOMA

(75) Inventors: Hans-Rainer Hoffmann, Neuwied (DE); Rudolf Matusch, Marburg (DE); Aria Baniahmad, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 45 days.

(21) Appl. No.: 11/883,415

(22) PCT Filed: Jan. 28, 2006

(86) PCT No.: PCT/EP2006/000746

§ 371 (c)(1),
(2), (4) Date: Jul. 31, 2007

(87) PCT Pub. No.: WO2006/081994

PCT Pub. Date: Aug. 10, 2006

(65) Prior Publication Data

US 2008/0177107 A1 Jul. 24, 2008

(30) Foreign Application Priority Data

Feb. 5, 2005 (DE) ................. 10 2005 005 397

(51) Int. Cl.
*A61K 31/18* (2006.01)
*C07C 311/16* (2006.01)
*C07C 311/17* (2006.01)

(52) U.S. Cl. .................. 514/604; 514/605; 564/87; 564/90; 564/93

(58) Field of Classification Search .......... 514/604, 514/605; 564/87, 90, 93
See application file for complete search history.

(56) References Cited

U.S. PATENT DOCUMENTS 4,069,254 A 1/1978 Hidaka et al.
5,891,454 A 4/1999 Wu et al.
2003/0022843 A1 1/2003 Wu et al.
2003/0208084 A1* 11/2003 Wu et al. ............... 548/534

FOREIGN PATENT DOCUMENTS

| DE | 2545496 | 3/1977 |
| DE | 2948186 | 7/1981 |
| EP | 1498099 | 3/2005 |
| GB | 2159815 | 12/1985 |
| WO | WO 95/26346 | 10/1995 |

OTHER PUBLICATIONS

Kim, KK; "Isolation and identification of antifungal N-Butylbenzenesulphonamide produced by Pseudomonas sp. AB2;" J. Antibiotics (2000); vol. 53, p. 131-136.
Beilstein Institut fur Literatur der organischen Chemie (Hrsg.): Beilsteins Handbuch der organischen Chemis, Drittes Erganzungswerk, 4, Aufl., Berling, 1972, Bd. 11, p. 54.
Strong, M.J.; In: Acta Neuropathol. (Berlin), 1991, vol. 81, p. 235-241 (Zusammenfassung).
Andro, Marie-Christine, et al.; "Pygeum africanum extract for the treatment of patients with benign prostatic hyperplasia: A review of 25 years of published experience;" *Current Therapeutic Research*; vol. 56, No. 8 (1995), pp. 796-817.
Debruyne, Frans, et al.; "Comparison of a Phytotherapeutic Agent (Permixon) with an alpha-blocker (Tamsulosin) in the treatment of benign prostatic hyperplasia: a 1-year randomized international study;" *European Urology*; May 2002, vol. 41, No. 5, pp. 497-506.
Hass, M.A., et al.; "Identification of Components of *Prunus africana* Extract that Inhibit Lipid Peroxidation;" *Phytomedicine*; Custav Fischer Verlag, Stuttgart, Germany, vol. 6, No. 5 (Nov. 1999), pp. 379-388.
Wu, Meihan, et al.; "Study on chemical components of essential oil in Foeniculum vulgare from different areas by GC—MS;" *Chemical Abstracts Service*; Columbus, Ohio.
Beilstein Institut fur Literatur der organischen Chemie (Hrsg.): Beilsteins Handbuch der organischen Chemis, Drittes Erganzungswerk, 4, Aufl., Berling, 1972, Bd. 11, p. 54.

* cited by examiner

*Primary Examiner*—Peter G O'Sullivan
(74) *Attorney, Agent, or Firm*—D. Peter Hochberg; Sean F. Mellino; Daniel J. Smola

(57) ABSTRACT

A process for isolating N-butylbenzenesulfonamide (NBBS) from biological material, the chemical synthesis of benzenesulfonamide derivatives, the use of NBBS and benzenesulfonamide derivatives for treating benign prostatic hyperplasia and/or prostate carcinoma, the production of medicaments for the treatment thereof, and the use of NBBS and benzenesulfonamide derivatives as a lead substance in the development of active substances for treating benign prostatic hyperplasia and/or prostate carcinoma are provided.

16 Claims, 6 Drawing Sheets

ISOLATION OF N-BUTYLBENZENESULFONAMIDE, SYNTHESIS OF BENZENESULFONAMIDE DERIVATIVES, AND USE OF N-BUTYLBENZENESULFONAMIDE AND BENZENESULFONAMIDE DERIVATIVES FOR TREATING BENIGN PROSTATIC HYPERPLASIA AND/OR PROSTATE CARCINOMA

CROSS-REFERENCE TO RELATED APPLICATIONS

This application is a National Stage application of International Application No. PCT/EP2006/000746, filed on Jan. 28, 2006, which claims priority of German application number 10 2005 005 397.1, filed on Feb. 5, 2005.

BACKGROUND OF THE INVENTION

1. Field of the Invention

The present invention relates to the treatment of benign prostatic hyperplasia and/or prostate carcinoma. More particularly, the present invention relates to a process for isolating N-butylbenzenesulfonamide (NBBS) from biological material, the chemical synthesis of benzenesulfonamide derivatives, the use of NBBS and benzenesulfonamide derivatives for treating benign prostatic hyperplasia and/or prostate carcinoma, the production of medicaments for the treatment thereof, and the use of NBBS and benzenesulfonamide derivatives as a lead substance in the development of active substances for treating benign prostatic hyperplasia and/or prostate carcinoma.

2. Description of the Prior Art

Benign enlargement of the prostate, also called benign prostate syndrome (BPS) or benign prostatic hyperplasia (BPH), and prostate cancer (also known as prostate carcinoma) are among the most common diseases affecting males as they age.

About 50% of men over the age of 60 years are afflicted by a benign form of prostate enlargement.

Benign prostatic hyperplasia is closely related to the development of prostate cancer, which is the most common cancer affecting men in middle age in the western countries and the second most common cause of cancer death in men.

BPH and prostate cancer are characterized, inter alia, by the progressive enlargement of the prostate. Enlargement of the prostate causes increasing narrowing (i.e., obstruction) of the urethra and obstruction of the bladder outlet, leading to problems when urinating. In the advanced stage the complete obstruction of the urethra, so-called anuria, leads to an emergency that requires immediate treatment.

The growth of the prostate is controlled by the male sex hormones, the androgens.

Several methods are available for the effective treatment of prostate carcinoma, amongst others, hormone therapy. Once the cancer has disseminated, a cure of prostate cancer is no longer possible. This applies to as many as one third of the patients at the time of the first diagnosis. In these cases, suppression of tumour growth and alleviation of the accompanying complaints are at the focus of the therapy. By suppressing the production of male sex hormones (testosterone) in order to counteract the transactivation function of the androgen receptor, it is possible to achieve temporary growth inhibition.

The major aim of the current therapies is to inactivate the androgen receptor (AR). The androgen receptor regulates male sex differentiation, is responsible for male fertility and promotes the growth of the normal prostate gland, but also promotes the proliferation of cancer cells of the prostate. Therefore, the androgen receptor has become an important target for prostate carcinoma therapy.

However, the current therapies are clearly limited since a prostate carcinoma will eventually exhibit resistance to this therapy.

The AR induces the expression of AR-responsive genes when it is bound to androgens. The inactivation of the androgen receptor is achieved either by reducing androgen synthesis or by administering androgen antagonists. So far, bicalutamide, flutamide, hydroxyflutamide (OH—F), nilutamide and cyproterone acetate (CPA) are used for the treatment of prostate cancer. These substances are administered with the aim of inactivating the transactivation of human androgen receptor.

However, eventually during the therapy the prostate carcinoma starts to regrow and exhibit resistance to the hormone deficiency. It has been found that androgen receptors are present and still remain active despite the treatment. The causes underlying this phenomenon remain largely unclear.

It is, however, apparent that there is a need for novel active substances for a successful treatment of BPH and/or prostate carcinoma.

Plant extracts for treating symptoms accompanying the enlargement of the prostate are traditionally wide-spread in many countries. The most commonly used extracts are those from the African plum tree (*Pygeum africanum*), which is also called *Prunus africana* (Hook. F.) Kalkm. according to more recent nomenclature, the Saw palmetto (*Serenoa repens*) and the pumpkin (*Cucurbita pepo*). The standardised lipophilic extracts from these plants contain sterols, saturated and unsaturated fatty acids as well as n-docosanol. The exact mechanism of action is yet unknown; it has been presumed, however, that the improvement of the symptoms associated with prostate enlargement is attributable to the sterol compound β-sitosterol, which is the quantitatively predominant component contained in the extracts.

Most of the clinical studies on the efficacy of extracts from the African plum tree were performed using chloroform extracts from its bark. This chloroform extract contains, inter alia, phytosterols, short-chain unsaturated fatty acids (lauric acid, myristic acid) and long-chain unsaturated fatty acids (oleic acid, linoleic acid. It is licensed under the designation TADENAN® in Italy, France and other European states, but not in Germany, for symptomatic treatment of BPH.

The placebo-controlled short-term studies using chloroform extracts from *P. africana* indeed showed a moderate clinical efficacy, but their concept was not even in accordance with the minimum requirements of the International Consultations on BPH. For this reason, a clear assessment of these studies is regrettably not possible.

SUMMARY OF THE PRESENT INVENTION

The object of the present invention is to provide novel active substances for the treatment of benign or malign prostate enlargement, i.e. benign prostatic hyperplasia and/or prostate carcinoma.

This object was achieved by isolating a substance having antiandrogenic activity from the bark of the African plum tree *P. africana*, and synthesising structural variants of these substances.

Surprisingly, the substance N-butylbenzenesulfonamide (NBBS) was isolated from the bark of *P. africana*, and it was found that this substance has a strong antiandrogenic activity.

NBBS is even able to inhibit the growth of prostate cancer cells that do not respond to treatment with hydroxyflutamide.

NBBS is a lipophilic substance that is used as a plasticiser in the production of polyamides and copolyamides and is also used in the synthesis of sulfonyl carbamate herbicides. NBBS is practically insoluble in water but exhibits moderate solubility in alcohols and benzene. NBBS is very stable and persists in the environment. Thus, NBBS was previously found in ground water, river water, in wine and in snow in concentrations up to 100 μg/l. Therefore, when using NBBS as an active substance in the treatment of BPH, there are hardly any toxicity problems to be expected.

However, on account of its antiandrogenic efficacy NBBS is a compound with which BPH and/or prostate cancer could be treated. NBBS may at least serve as a lead substance in the development of new active substances for the treatment of BPH and/or prostate carcinoma.

The object of providing novel antiandrogenic active substances for treating benign prostate hyperplasia and/or prostate carcinoma is also achieved by providing sulfonamide derivatives of NBBS wherein the butyl side chain and the benzene ring have been modified by substituents.

DETAILED DESCRIPTION OF THE INVENTION

Figure 1:
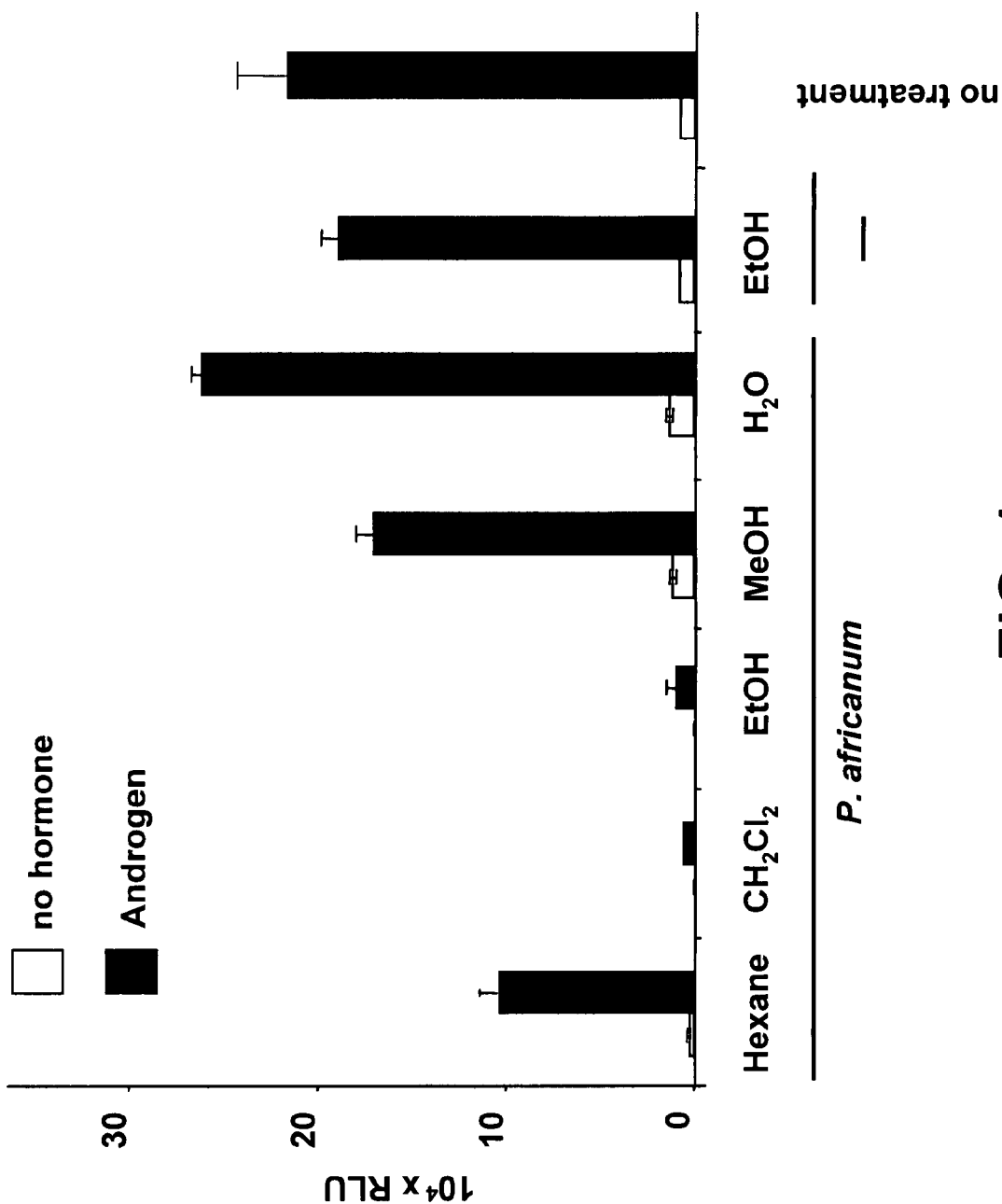
FIG. 1 shows the inhibition of the activity of an androgen by different extracts of P. africana.

To be able to identify the component or a component from the bark of P. africana that is effective in the treatment of BPH and/or prostate carcinoma, the bark was selectively extracted with various solvents and the extracts obtained were examined for antiandrogenic activity by measuring their potency for inhibiting the activity of the human, hormone-activated androgen receptor in a reporter gene-based test. The results of this test are shown in FIG. 1.

It was found that the water extract and the methanol extract of P. africana bark revealed no antiandrogenic activity in the test. The selective hexane extract only lead to approximately half of the androgen-induced luciferase activity compared to the controls, which were not treated with an extract.

The ethanol extract and the methylene chloride extract prevented androgen-induced luciferase activity in the tests almost completely. These two extracts showed the highest biological activity.

Figure 2:
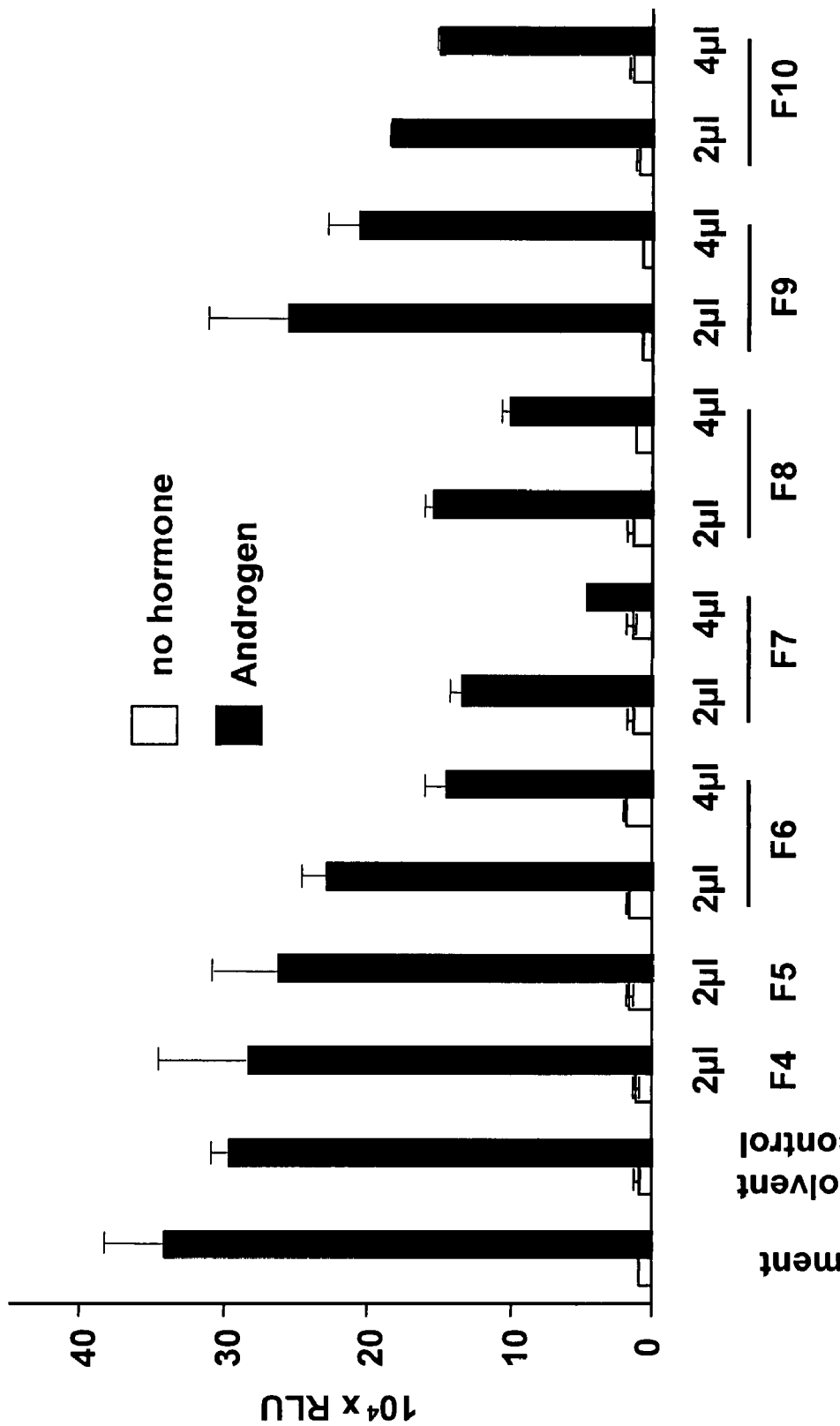
FIG. 2 shows the antiandrogenic effect of fractions of the selective methylene chloride extract of P. africana.

To further identify antiandrogenic active substances from P. africana, the selective methylene chloride extract was fractionated using silica gel chromatography. The resulting fractions were again tested for their antiandrogenic action in the reporter gene-based test. Part of the results of this test is shown in FIG. 2. Especially the fractions F7 and F8 showed an antiandrogenic effect in the cell culture test.

Both fractions were used for further analysis. By means of preparative HPLC, N-butylbenzenesulfonamide was isolated from fraction F8, as was shown by the analytical data.

Figure 3:
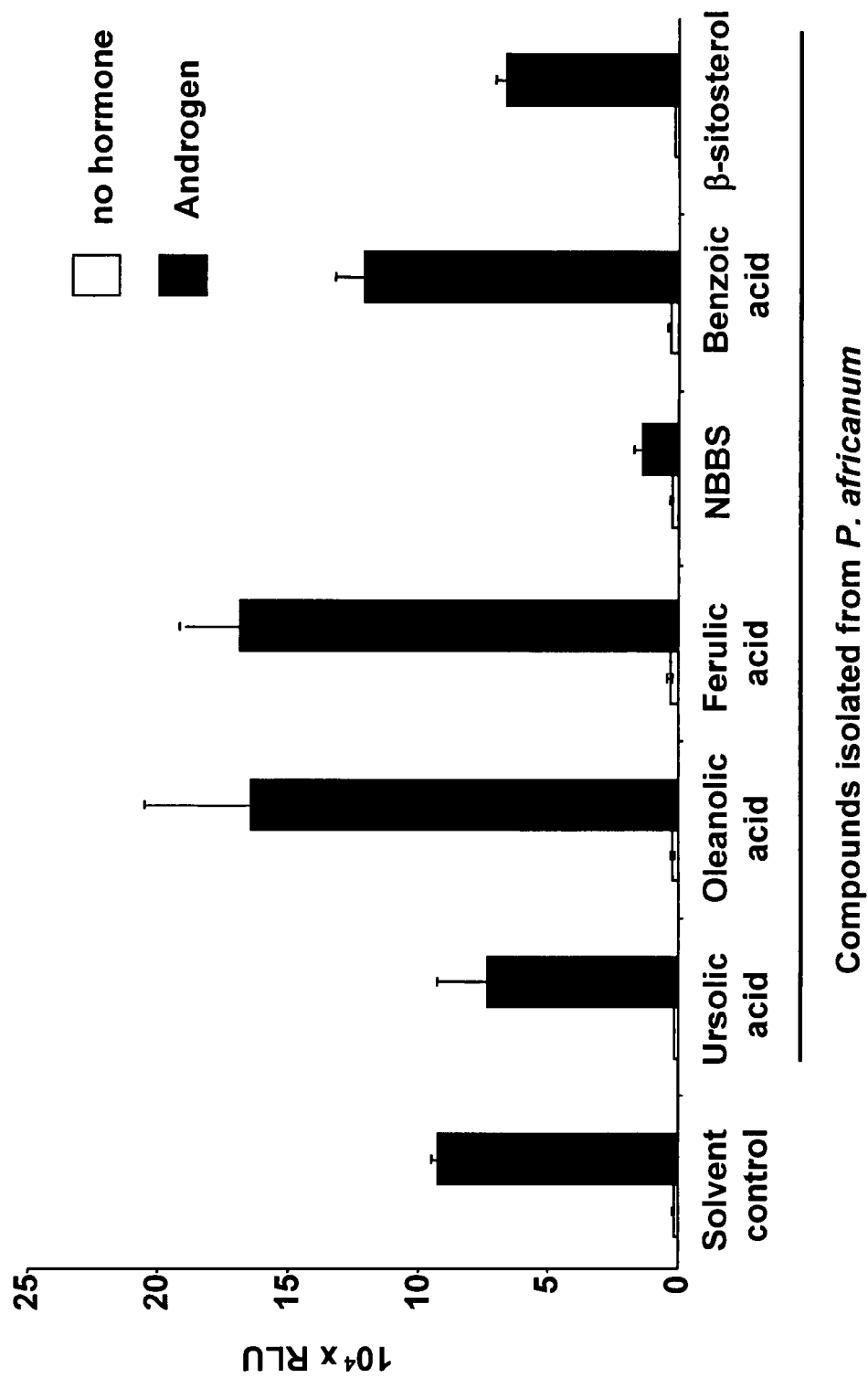
FIG. 3 shows a comparison of the antiandrogenic effect of compounds contained in P. africana.

N-butylbenzenesulfonamide inhibited the androgen-induced luciferase effect in the cell culture test (see FIG. 3). The activity of NBBS was compared with the effect of the compounds ursolic acid, oleanolic acid, ferulic acid, benzoic acid and β-sitosterol, which are also contained in P. africana and which are being discussed as being responsible, or which at least were possible candidates, for the efficacy of the known plant-derived drug (TADENAN®), which is extracted from P. africana. The results of this comparative test are shown in FIG. 3.

With the exception of β-sitosterol, none of the comparison compounds had any significant influence on the androgen-induced reporter gene activity.

N-butylbenzenesulfonamide has an antiandrogenic activity that is higher than the antiandrogenic activity of the substances from P. africana that are taken into consideration as being the cause of the efficacy of the standardised chloroform extract from this plant species.

The present invention thus relates to the use of NBBS for treating benign prostate hyperplasia and for the manufacture of a medicament for treating benign prostate hyperplasia.

Figure 4:
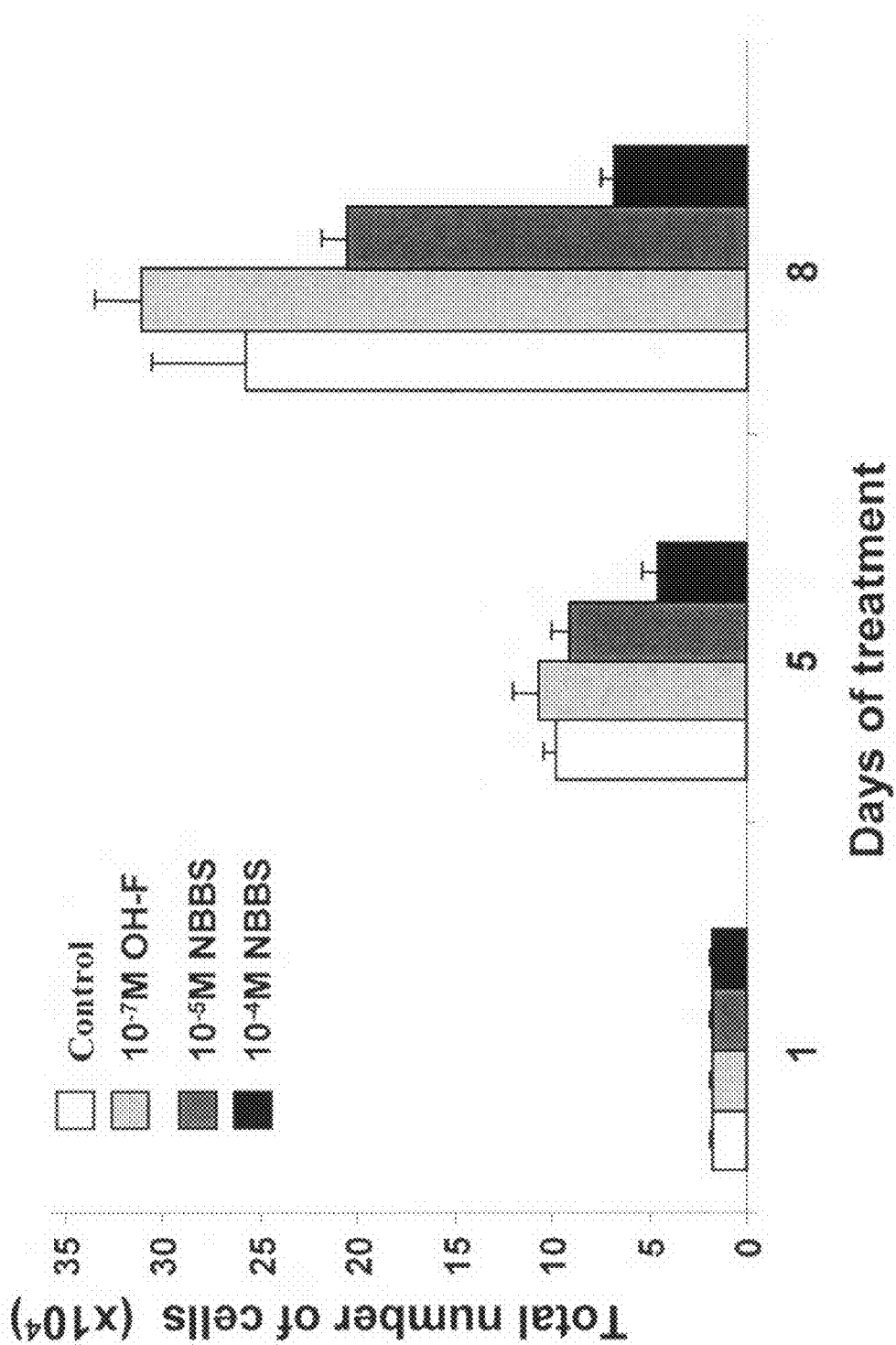
FIG. 4 illustrates the inhibition of the growth of human prostate carcinoma cells by NBBS.

The growth of prostate cells and prostate cancer cells is originally dependent on androgens. To test whether the androgen antagonism of NBBS also affects cell growth, the human prostate cancer cell line LNCaP was used, whose growth is known to be androgen dependent. LNCaP cells were cultured in the presence of NBBS. FIG. 4 shows that already on day 5 of treatment, the cells treated with 100 μM NBBS exhibited a markedly slower proliferation than the untreated cells. This effect was even more prominent on day 8 of the treatment. In the presence of 10 μM NBBS, too, the LNCaP cells exhibited a reduced growth on day 8 of treatment, whereas the treatment with OH—F did not lead to reduction in cell proliferation. The latter may be due to LNCaP cells having a point mutation in the ligand binding domain of the human AR that prevents OH—F from acting as an antiandrogen in these cells.

These data show that the androgen antagonism of NBBS is also effective for a mutated human androgen receptor. Thus, NBBS is able to inhibit growth of LNCaP cells. Consequently, NBBS could also be used to treat prostate carcinomas that are resistant to known antiandrogenic active agents such as hydroxyflutamide.

The present invention thus also relates to the use of NBBS for treating prostate carcinoma and for the manufacture of a medicament for treating prostate carcinoma, particularly of prostate carcinomas that are resistant to any treatment with known androgen antagonists such as, for example, bicalutamide, flutamide, hydroxyflutamide, nilutamide or cyproterone acetate.

A further subject matter of the invention is the use of NBBS as a lead substance in the development of novel active substances for treating benign prostatic hyperplasia and/or prostate carcinoma.

The present invention further relates to a method of isolating NBBS from biological material, particularly from the bark of the African plum tree P. africana.

In the method of the present invention, the plant material is initially reduced to small pieces, then extracted with a solvent in which NBBS is soluble, and NBBS is purified from the resulting extract, for example by fractionation employing suitable chromatography methods and separating NBBS from the fractions containing that substance by removing the solvent.

Extraction is preferably performed as a selective extraction by a series of successive solvents with increasing polarity. The fractionation of the extract is preferably performed by gradient extrography, with increasing polarity of the eluents. Isolation of NBBS may subsequently take place by preparative HPLC from the fractions containing NBBS.

In this way, it was possible to isolate the antiandrogenic, lipophile substance NBBS from the selective methylene chloride extract. As was shown by analyses, NBBS was also contained in the ethanol extract, which likewise exhibited antiandrogenic action.

Solvents suitable for the extraction of NBBS from plant material are therefore the solvents selected from the group comprising univalent $C_1$ to $C_4$ alcohols (alcohols with one to four carbon atoms), and high-volatile, (partially) halogenated $C_1$ hydrocarbons, preferably methylene chloride and chloroform.

The preferred chromatographic method is column chromatographic fractionation by silica gel, and preparative HPLC.

The object of providing novel active substances for treating benign prostatic hyperplasia and/or prostate carcinoma was also achieved by synthesizing further structural variants of this compound on the basis of NBBS isolated from *P. africana*.

The synthesis of structural variants of NBBS was started directly from arylsulfonic acid chloride and the primary aliphatic amine. The reaction of an acid chloride with the amine could take place without a solvent, simply by mixing the two components in a mortar using a pestle. However, since in the case of the NBBS structural variants both starting compounds were mostly present in liquid form, a three-neck flask with a stirrer, reflux cooler, thermometer and dripping funnel were preferred. An excessive amount of amine was used, and the sulfonic acid chloride was slowly added in drops while stirring. The reaction is highly exothermic and takes place quantitatively. After cooling of the reaction mixture, water was added, and the reaction product was shaken out with dichloromethane. The progress of the reaction was monitored by thin-layer chromatography.

The ratio of amine:sulfonic acid chloride was 2:1 in the reactions. In the case of the gaseous amines methyl amine and ethyl amine, an aqueous solution was used and four times the equivalent of amine, compared to the acid chloride, was used.

In this reaction of a primary aliphatic amine with a sulfonic acid chloride, the free electron pair attacks as nucleophiles at the sulfur of the sulfonic acid chloride. Apart from the reaction product, this also produces hydrochloric acid, which protonates the excessive amine. The amine salt remains in the aqueous phase when the sulfonamide is shaken out with dichloromethane, and can thus be separated.

Figure 5:
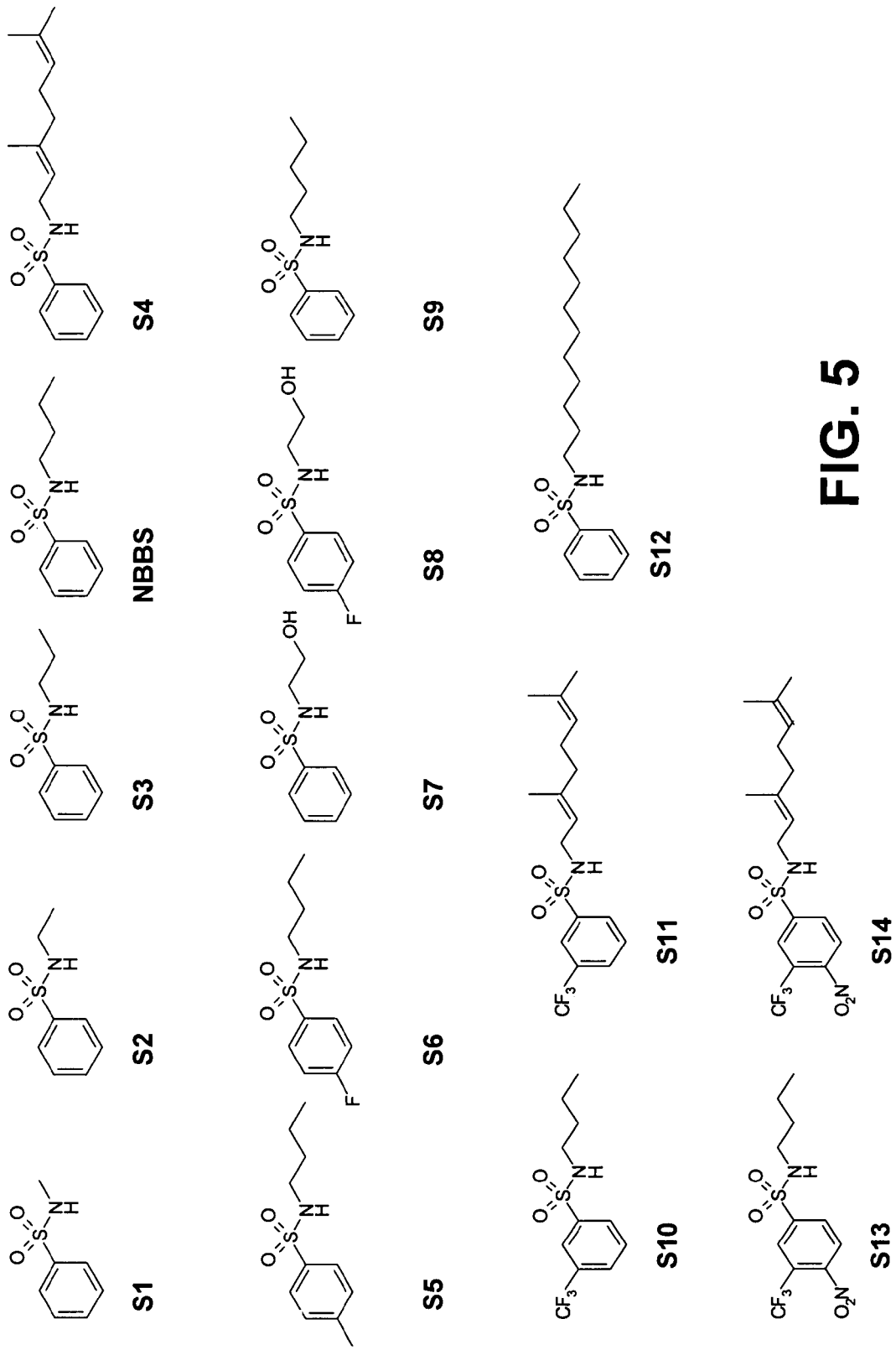
FIG. 5 indicates the structural formula of the synthesised benzenesulfonamide derivatives.

In this manner, a series of N-monoalkylbenzenesulfonamides with different alkyl chains was initially prepared. The liquid benzenesulfonic acid chloride and the corresponding primary amine component were used as the starting materials. The structural formulas of the sulfonamides with variable alkyl chain are indicated in FIG. 5. N-geranyl-benzenesulfonamide (S4) is also shown there. This substance was synthesized because enhanced membrane permeability was hoped for on account of the terpenoid side chain.

The next series of synthesised sulfonamides comprises both the introduction of substituents at the aromatic (S5 and S6) and variation of the aminoalkyl chain with a terminal hydroxyl group (S7 and S8).

The compounds S5 and S6 were produced starting from 4-toluenesulfonic acid chloride and 4-fluorobenzenesulfonic acid chloride with N-butylamine in the same manner as the compounds S1 to S7, S9 and S12.

The synthesis of the compounds S7 and S8 could not be performed in this manner since here the hydroxyl group of the ethanolamine used competes with the amino group. Thus, apart from the sulfonic acid amide there is also produced a certain amount of sulfonic acid ester.

However, the synthesis of S7 and S8 succeeded by initially treating one equivalent of benzenesulfonic acid chloride and 4-fluorobenzenesulfonic acid chloride, respectively, with 2.2 equivalents of ethanolamine in ortho-xylene for five hours under reflux. After completion of the reaction, a viscous liquid settled at the bottom; this liquid was separated. The liquid was the sulfonamide that, on account of the excess of amine and its acidic character, is present in deprotonated form and thus separates from the organic phase. By contrast, the sulfonic acid ester does not have acidic properties and remains dissolved in the xylene phase. Then, aqueous alkali was added to the separated sulfonamide until a clear solution was obtained. By acidifying with concentrated hydrochloric acid, the sulfonamide settled again in purified form as yellow syrup. After separating the sulfonamide, acetone was added thereto. The sulfonamide was thereby dissolved, and the sodium chloride, which had formed in the acidifying step and had coprecipitated, remained as bottom sediment and could be removed by filtration. The acetone was removed in the rotary evaporator, and the purified product was obtained.

The third series of structural variants of NBBS was oriented on the structure of the antiandrogenic substance 2-hydroxyflutamide. 2-Hydroxyflutamide is the active metabolite of flutamide (FUGEREL®).

Introducing a trifluoromethyl group at the meta-position enhances the lipophilicity of the molecule. This should ensure an improved ability to penetrate the cell membrane. The additional nitro group in S13 and S14 at the para-position results in a further improvement of the lipophilic properties. The geranyl side chain is to improve anchorage in biological membranes.

The synthesis of S10 to S14 was performed starting from 3-trifluoromethylbenzenesulfonamide and 4-nitro-3-trifluoromethylbenzenesulfonamide, respectively, and N-butylamine and N-geranylamine, respectively.

4-Nitro-3-trifluoromethylbenzenesulfonamide is solid at room temperature, so that dichloromethane had to be used as the solvent.

Figure 6:
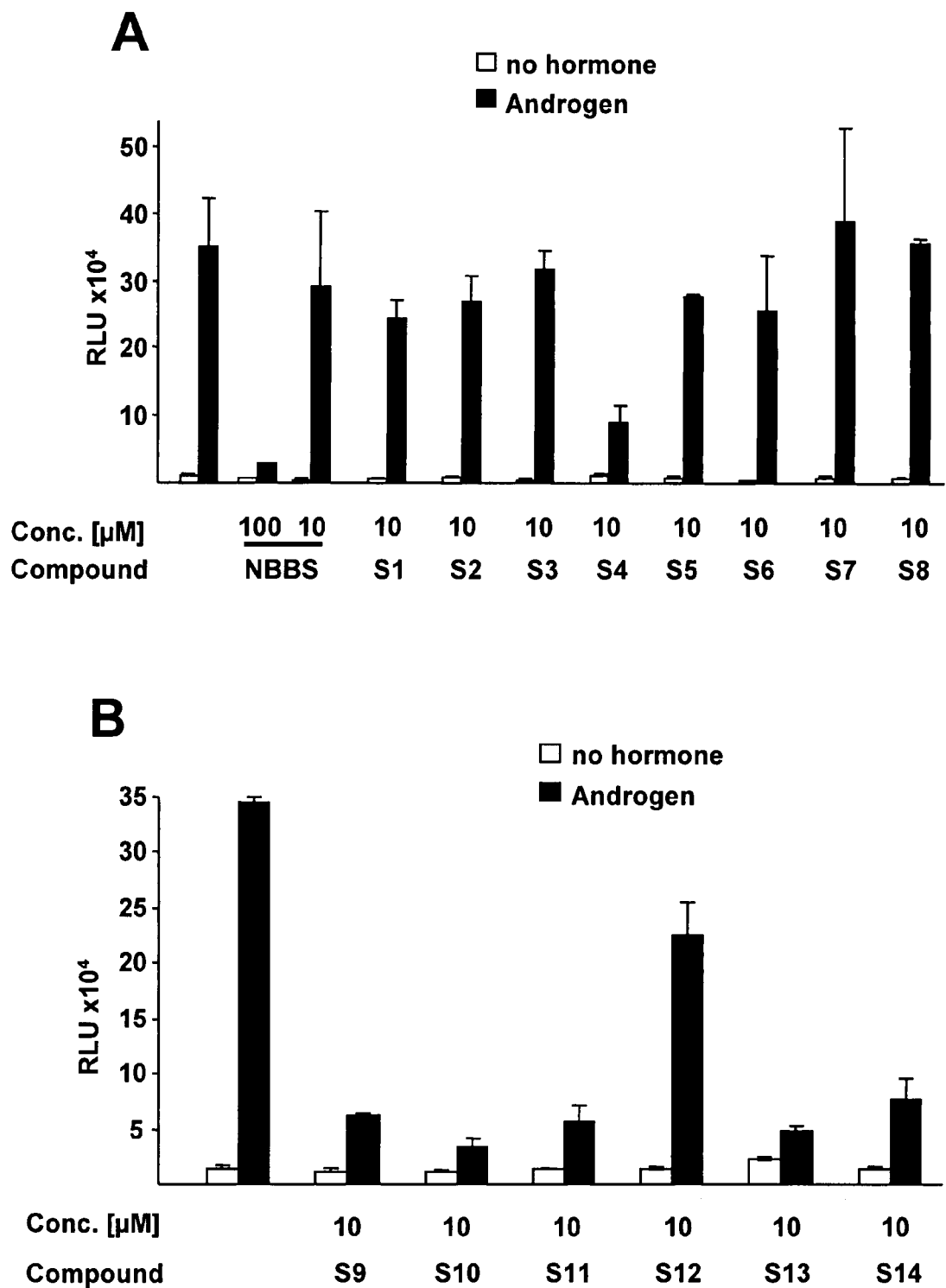
FIG. 6 shows a diagram illustrating the antiandrogenic effect of the synthesised benzenesulfonamide derivatives.

To examine the efficacy of the benzenesulfonamide derivatives with respect to an inhibition of the AR-mediated transactivation, each of the synthesized compounds was compared at a concentration of 10 µM with the efficacy of NBBS (FIG. 6). A high concentration ($3\times10^{-8}$M) of R1881 was used, at which 10 µM of NBBS showed no specific inhibition of the AR-mediated transactivation.

The compounds S1 to S3 and S5 to S8 at the concentration employed showed no significant antiandrogenic action that exceeded the antiandrogenic action of NBBS. The modifications of the compounds S1 to S3 and S5 to S8 included either shortening the butyl side chain (S1 to S3 and S7) or a substitution of the benzene ring at the para-position (S5, S6 and S8). The results on the antiandrogenic efficacy of these compounds reveal the importance of the length of the side chain and of the presence of a benzene ring that is unsubstituted at the para-position for the antiandrogenic effect of benzenesulfonamide derivatives.

Surprisingly, lengthening the side chain by replacing the butyl side chain with a pentyl or a geranyl group (S4 and S9) enhanced the antiandrogenic activity, indicating that a hydrophobic side chain is important for antiandrogenic activity. However, further extension of the side chain by introducing a lauryl group (S12) weakened the androgen antagonistic potency. Therefore, enhancing the hydrophobicity alone is not sufficient to enhance the antiandrogenic efficacy of NBBS.

Surprisingly, also substitutions at the meta-position of the benzene ring enhanced antiandrogenic activity (S10, S11, S13 and S14), with an additional substitution at the benzene ring in para-position not significantly affecting the increased antiandrogenic activity of the compounds with a substitution at the meta-position, as demonstrated by a comparison of the antiandrogenic effects of substance S14 with S11, and S13 with S10.

The subject matter of the present invention is therefore a process for the production of benzenesulfonamide derivatives of the formula

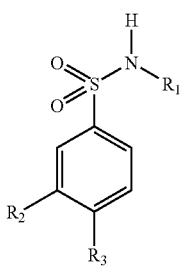

wherein $R_1$ represents an aliphatic $C_1$ to $C_{12}$ hydrocarbon, $R_2$ is hydrogen or a completely or partially halogenated $C_1$ residue, and $R_3$ is hydrogen or a nitro group. The process includes a benzenesulfonic acid derivative of the formula

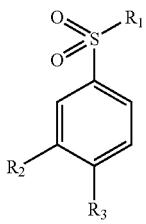

wherein $R_1$ represents halogen, $R_2$ hydrogen or a completely or partially halogenated $C_1$-residue, and $R_3$ is hydrogen or a nitro group, is converted with a primary aliphatic amine, and the reaction product is shaken out with dichloromethane, with the primary aliphatic amine preferably being selected from the group comprising $C_1$ to $C_{12}$ aliphatic hydrocarbons. Butylamine or geranylamine is used with particular preference as the primary aliphatic amine.

The reaction product can also be shaken out with ether to prevent the synthetic compounds from failing to gain drug approval because halogenated solvents were used.

"Aliphatic" is to be understood to mean organic compounds whose carbon atoms are arranged in straight or branched chains and which may contain saturated and/or unsaturated C—C bonds and/or functional groups, but also organic compounds containing only one carbon atom.

A further subject matter of the present invention are therefore benzenesulfonamide derivatives for treating benign prostatic hyperplasia and/or prostate carcinoma of the formula

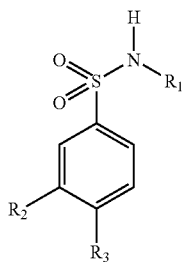

wherein $R_1$ represents an aliphatic $C_1$ to $C_{12}$ hydrocarbon, $R_2$ hydrogen or a completely or partially halogenated $C_1$ residue, and $R_3$ is hydrogen or a nitro group.

Insofar, the present invention also relates to the use of a benzenesulfonamide derivative of the formula

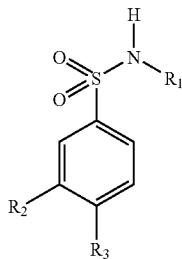

wherein $R_1$ represents an aliphatic $C_1$ to $C_{12}$ hydrocarbon, $R_2$ hydrogen or a completely or partially halogenated $C_1$ residue, and $R_3$ is hydrogen or a nitro group, for the treatment of benign prostatic hyperplasia and/or prostate carcinoma and for the production of a medicament for the treatment thereof, and as a lead substance for developing further/novel active substances for the treatment of benign prostatic hyperplasia and/or prostate carcinoma, especially for treating the prostate carcinoma that is resistant to a therapy with androgen antagonists.

A further subject matter of the invention are pharmaceutical preparations for the treatment of benign prostatic hyperplasia and/or prostate carcinoma that contain at least one benzenesulfonamide derivative of the formula

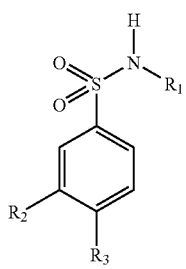

wherein $R_1$ represents an aliphatic $C_1$ to $C_{12}$ hydrocarbon, $R_2$ is hydrogen or a completely or partially halogenated $C_1$ residue; and R3 is hydrogen or a nitro group.

EXAMPLE 1

Extraction of the Plant Material

Dried bark of the African plum tree (*P. africanum*) was powdered, and 1.73 kg of the powdered bark were homogenized in 1 l n-hexane (ice-cooling) using an ULTRA TURRAX®. The plant material was filled into a column (Merck PREPBAR® 400×100 mm) and selectively extracted successively with 25.0 l of n-hexane, 26.0 l of methylene chloride, 25.0 l of methanol (MeOH) and 12.5 l of water at room temperature. The solvents of the resulting extracts were evaporated in vacuo at 40° C. This yielded 4.80 g selective hexane extract, 11.03 g selective methylene chloride extract, 116.81 g selective methanol extract and 7.00 g selective water extract.

For preparing an ethanolic extract, 300.00 g bark material of *P. africanum* was powdered and extracted three times, each time with 5.0 l ethanol (EtOH). After filtering the extract through filter paper of 0.7 μm pore size, the solvent was removed from the entire extract at 40° C. using a rotary evaporator. The dried mass of the resulting extract was 16.02 g.

EXAMPLE 2

Fractionation of the Methylene Chloride Extract

The selective methylene chloride extract of *Pygeum africanum* was fractionated with silica gel (Macherey-Nagel Si60, 15-25 μm). For this purpose the extract was dissolved in 2000 ml $CH_2Cl_2$ and filtered through filter paper with a pore size of 0.7 μm (Schleicher & Schüll). 25 g of silica gel (Merck Si60, 0.063-0.2 mm) was added to the extract and then the solvent was evaporated in vacuo at 40° C. The thus-coated silica gel was placed on the top of a dry packed silica gel column (Merck PREPBAR® 400×100 mm) and eluted, with a flow rate of 120 ml·min$^{-1}$, with a linear gradient of 0 min hexane (100:0), 50 min hexane (100:0), 350 min $CH_2Cl_2$ (100:0), 500 min $CH_2Cl_2$ (100:0), 700 min $CH_2Cl_2$—MeOH (80:20), 750 min MeOH (100:0), 800 min MeOH (100:0), 850 min $H_2O$ (100:0), 885 min $H_2O$ (100:0). The chromatography gave 35 fractions which led to detection by UV light at a wavelength of 245 nm (Table 1).

TABLE 1

Fractionation of the selective methylene chloride extract of *P. africana*

| Fraction | Min | Mass (mg) |
| --- | --- | --- |
| F1 | 0-148 | 3 |
| F2 | 149-184 | 52 |
| F3 | 185-204 | 33 |
| F4 | 205-229 | 63 |
| F5 | 230-238 | 14 |
| F6 | 239-261 | 61 |
| F7 | 262-266 | 30 |
| F8 | 267-293 | 243 |
| F9 | 294-331 | 380 |
| F10 | 332-338 | 17 |
| F11 | 339-356 | 164 |
| F12 | 357-369 | 119 |
| F13 | 370-373 | 38 |
| F14 | 374-375 | 71 |
| F15 | 376-562 | 110 |
| F16 | 563-581 | 44 |
| F17 | 582-592 | 24 |
| F18 | 593-614 | 1537 |
| F19 | 615-630 | 799 |
| F20 | 631-638 | 292 |
| F21 | 639-659 | 1338 |
| F22 | 660-663 | 20 |
| F23 | 664-671 | 327 |
| F24 | 672-692 | 634 |
| F25 | 693-703 | 157 |
| F26 | 704-724 | 333 |
| F27 | 725-749 | 350 |
| F28 | 750-771 | 393 |
| F29 | 772-784 | 316 |
| F30 | 785-803 | 141 |
| F31 | 804-820 | 57 |
| F32 | 821-828 | 58 |
| F33 | 829-836 | 1 |
| F34 | 837-858 | 126 |
| F35 | 859-880 | 1 |

EXAMPLE 3

Isolation of N-butylbenzenesulfonamide

NBBS was isolated from fraction F8 by preparative HPLC (250×21 mm, 100-5 C18 HD Macherey-Nagel, 22 ml·min$^{-1}$, UV detection at 220 nm, Gradient: 0 min ACN-$H_2O$ (with addition of 0.1% of TFA) ((20:80), 40 min ACN-$H_2O$ (80:20), 45 min ACN (100:0)). NBBS was collected from min 12.6 to min 14.0. Its structure was elucidated on the basis of the $^1$H and $^{13}$C NMR, EI-MS, HR-EI-MS, IR and UV spectra.

EXAMPLE 4

Cell Culture and Luciferase Assay

Monkey kidney cells, line CV1, lacking endogenous androgen receptor were cultured in Dulbecco's modified Eagle's medium (DMEM), supplemented with 10% (v/v) fetal calf serum, penicillin (100 IU/ml) and streptomycin (100 IU/ml) at 37° C. and 5% $CO_2$.

For the transfection experiments, cells were seeded onto 6-well tissue culture plates (Nunc, Roskilde, Denmark) with a density of 1.2×10$^5$ cells per well and grown in DMEM medium supplemented with 10% (v/v) dextran-coated activated charcoal stripped serum. Six hours after seeding, the cells were transfected by using the $Ca_3(PO_4)_2$ method. The human androgen receptor (hAR) expression vector (0.2 μg) was cotransfected with 1 μg of the reporter plasmid MMTV-luc and 0.2 μg of the cytomegalovirus (CMV)-driven β-galactosidase expression virus, as internal control for transfection efficiency. After 14 hours, the medium was replaced either without (white bars in FIGS. 1 to 3) or with the addition of methyltrienolone (R1881, 3×10$^{-10}$ M final concentration; black bars in FIGS. 1 to 3) together with the indicated extracts (FIG. 1), fractions (FIG. 2) or substances (FIG. 3). After an additional 48 hours, cells were harvested and assayed for luciferase and β-galactosidase activity.

Luciferase activity was determined by injecting luciferin and measuring light emission at 562 nm and expressed as relative light units (RLU) by using the values of β-galactosidase activity for normalisation of the luciferase activity. All transfection assays shown were performed in duplicate and were repeated at least twice.

For determining antiandrogenic activity in the various extracts from the bark of *P. africanum*, the extracts were used at a concentration of 300 µg/ml. The results are shown in FIG. 1.

For determining the antiandrogenic activity in the fractions of the selective methylene chloride extracts, 2 µl of the respective fraction was used, corresponding to a final concentration of 30 µg/ml. Fractions F6 to F10 were additionally tested with 4 µl, corresponding to 60 µg/ml final concentration. Active fractions F7 and F8 were used for the further tests. Part of the results is shown in FIG. 2.

For a comparison of antiandrogenic activity of compounds of *P. africanum*, cells were cultured in the presence of β-sitosterol, benzoic acid, NBBS, ferulic acid, oleanolic acid or ursolic acid at $10^{-5}$ M final concentration in the cell culture medium, and in the presence of or without methyltrienolone ($3 \times 10^{-10}$ M). The results are indicated in FIG. 3.

EXAMPLE 5

Growth Inhibition of Human Prostate Carcinoma Cells by NBBS

Human prostate carcinoma cells (cell line LNCaP) were cultured in RPMI-1640 medium, supplemented with 10% (v/v) fetal calf serum, penicillin (100 IU/ml) and streptomycin (100 IU/ml), 2 mM glutamine and 1 mM sodium pyruvate.

For the cell growth assays LNCaP cells were seeded onto a 24-well tissue culture plate at a density of $5 \times 10^3$ cells per well and cultured in RPMI-1640 medium containing 5% fetal calf serum. On day 2, the culture medium was replaced, and ethanol/DMSO (control), NBBS (10 µM and 100 µM) or the known antiandrogen hydroxyflutamide (OH—F) (0.1 µM) was added to treat the cells. Every second day the medium and additives were replaced with fresh media together with freshly added compounds. The cells were trypsinized and counted using a counting cell chamber on the indicated days.

EXAMPLE 6

Synthesis of Methylbenzene Sulfonamide (=S1)

IUPAC: N-Methylbenzenesulfonamide
Empirical formula: $C_7H_9NO_2S$ (MW=171.04)
Synthesis:
17.662 g of benzenesulfonic acid chloride (0.1 mol) were added in drops to 31.06 g of an aqueous solution (40%) of methylamine (0.4 mol) while stirring. After cooling of the reaction mixture, 20 ml of water were added, and the reaction product was shaken out with dichloromethane ($3 \times 20$ ml). The combined organic phases were washed with water ($2 \times 20$ ml) and narrowed down on the rotary evaporator at reduced pressure.
Appearance: colourless oil
Yield: 15.940 g (93%) UV (MeOH) $\lambda_{max}$ nm: 220, 265 IR (KBr) $v_{ax}$ cm$^{-1}$: 3300, 3070, 2980, 1450, 1320, 1160 $^1$H-NMR (500 MHz, CDCl$_3$), δ (ppm): 7.80 (2H, d, $^3$J=7.5 Hz, C-2-H und C-6-H) 7.51 (1H, t, $^3$J=6.5 Hz, C-4-H) 7.45 (2H, t, $^3$J=6.5 Hz, C-3-H und C-5-H) 4.87 (1H, s, N—H) 2.57 (3H, s, C-1'-H) $^{13}$C-NMR (125 MHz, CDCl$_3$), δ (ppm): 138.8 (C-1) 29.3 (C-1') 132.7 (C-4) 129.1 (C-3 und C-5) 127.2 (C-2 und C-6) EI-MS (70 eV): m/z (rel. int.): 171 [M]$^+$ (81), 141 (52), 77 (100) High-accuracy mass determination (HR-EI-MS): Calculated: 171.0354 for [M]$^+$ Found: 171.0338.

EXAMPLE 7

Synthesis of Ethylbenzenesulfonamide (=S2)

IUPAC: N-ethylbenzenesulfonamide
Empirical formula: $C_8H_{11}NO_2S$ (MW=185.05)
Synthesis:
17.662 g of benzenesulfonic acid chloride (0.1 mol) were added in drops to 25.76 g of an aqueous solution (70%) of ethylamine while stirring. After cooling of the reaction mixture 20 ml of water were added, and the reaction product was shaken out with dichloromethane ($3 \times 20$ ml). The combined organic phases were washed with water ($2 \times 20$ ml) and narrowed down on the rotary evaporator at reduced pressure.
Appearance: Colourless crystals
Yields: 17.373 g (94%) Melting point (° C.): 51 UV (MeOH) $\lambda_{max}$ nm: 220, 264 IR (KBr) $v_{max}$ cm$^{-1}$: 3300, 2980, 2940, 1450, 1320, 1160 $^1$H-NMR (500 MHz, CDCl$_3$), δ (ppm): 7.81 (2H, d, $^3$J=8.0 Hz, C-2-H und C-6-H) 7.51 (1H, t, $^3$J=6.2 Hz, C-4-H) 7.45 (2H, t, $^3$J=6.9 Hz, C-3-H und C-5-H) 4.43 (1H, s, N—H) 2.95 (2H, q, $^3$J=6.0 Hz, C-1'-H) 1.04 (3H, t, $^3$J=5.5 Hz, C-2'-H) $^{13}$C-NMR (125 MHz, CDCl$_3$), δ (ppm): 140.0 (C-1) 38.2 (C-1') 132.5 (C-4) 15.0 (C-2') 129.0 (C-3 und C-5) 127.0 (C-2 und C-6) EI-MS (70 eV): m/z (rel. int.): 185 [M]$^+$ (67), 170 (100), 141 (87), 77 (55) High-accuracy mass determination: (HR-EI-MS): Calculated: 185.0511 for [M]$^+$ Found: 185.0512.

EXAMPLE 8

Synthesis of Propylbenzenesulfonamide (=S3)

IUPAC: N-Propylbenzenesulfonamide
Empirical formula: $C_9H_{13}NO_2S$ (MW=199.07)
Synthesis:
8.831 g of benzenesulfonic acid chloride (0.05 mol) were added in drops to 11.822 g of propylamine (0.2 mol) while stirring. After cooling of the reaction mixture, 20 ml of water were added, and the reaction product was shaken out with dichloromethane ($3 \times 20$ ml). The combined organic phases were washed with water ($2 \times 20$ ml) and narrowed down on the rotary evaporator at reduced pressure.
Appearance: yellow oil
Yield: 9.517 g (96%) UV (MeOH) $\lambda_{max}$ nm: 220, 265 IR (KBr) $v_{max}$ cm$^{-1}$: 3290, 2970, 2940, 1450, 1320, 1160 $^1$H-NMR (500 MHz, CDCl$_3$), δ (ppm): 7.81 (2H, d, $^3$J=7.5 Hz, C-2-H und C-6-H) 7.50 (1H, t, $^3$J=3.3 Hz, C-4-H) 7.45 (2H, t, $^3$J=3.0 Hz, C-3-H und C-5-H) 4.81 (1H, s, N—H) 2.84 (2H, q, $^3$J=4.0 Hz, C-1'-H) 1.42 (2H, m, $^3$J=7.5 Hz, C-2'-H) 0.78 (3H, t, $^3$J=4.5 Hz, C-3'-H) $^{13}$C-NMR (125 MHz, CDCl$_3$), δ (ppm): 140.1 (C-1) 45.0 (C-1') 132.5 (C-4) 23.0 (C-2') 129.1 (C-3 und C-5) 11.0 (C-3') 127.0 (C-2 und C-6) EI-MS (70 eV): m/z (rel. int.): 199 [M]$^+$ (39), 170 (100), 141 (84), 77 (51) High-accuracy mass determination (HR-EI-MS): Calculated: 199.0667 for [M]$^+$ Found: 199.0666.

EXAMPLE 9

Synthesis of Geranylbenenesulfonamide (=S4)

IUPAC: N-[(2E)-3,7-Dimethylocta-2,6-diene-1-yl]benzenesulfonamide
Empirical formula: $C_{16}H_{23}NO_2S$ (MW=293.14)
Synthesis:

177 mg of benzenesulfonic acid chloride (1 mmol) were added in drops to 307 mg of geranylamine (2 mmol) while stirring. After cooling of the reaction mixture, 10 ml of water were added, and the reaction product was shaken out with dichloromethane (3×10 ml). The combined organic phases were washed with 0.1 mM of hydrochloric acid (3×5 ml) and narrowed down on the rotary evaporator at reduced pressure.

Appearance: brownish oil

Yield: 281 mg (96%) UV (MeOH) $\lambda_{max}$ nm: 205, 221, 264 IR (KBr) $v_{max}$ cm$^{-1}$: 3280, 2900, 1450, 1330, 1160 $^1$H-NMR (500 MHz, CDCl$_3$), δ (ppm): 7.82 (2H, d, $^3J$=7.0 Hz, C-2-H und C-6-H) 7.51 (1H, t, $^3J$=6.4 Hz, C-4-H) 7.45 (2H, t, $^3J$=7.6 Hz, C-3-H und C-5-H) 4.95 (2H, m, $^3J$=7.0 Hz, C-2'-H und C-6'-H) 4.31 (1H, t, $^3J$=6.0 Hz, N—H) 3.52 (2H, q, $^3J$=6.5 Hz, C-1'-H) 1.90 (2H, q, $^3J$=8.0 Hz, C-5'-H) 1.84 (2H, t, $^3J$=8.0 Hz, C-4'-H) 1.60 (3H, s, C-3'-Me) 1.50 (3H, s, C-7'-Me) 1.46 (3H, s, C-8') $^{13}$C-NMR (125 MHz, CDCl$_3$), δ (ppm): 141.3 (C-3') 127.1 (C-2 und C-6) 26.2 (C-8') 140.1 (C-1) 123.6 (C-2') 25.6 (C-7'-Me) 132.6 (C-7') 118.5 (C-6') 17.7 (C-5') 131.9 (C-4) 41.0 (C-1') 16.2 (C-3'-Me) 129.0 (C-3 und C-5) 39.3 (C-4') EI-MS (70 eV): m/z (rel. int.): 293 [M]$^+$ (47), 210 (72), 170 (100), 152 (83), 141 (80), 77 (46) High-accuracy mass determination (HR-EI-MS): Calculated: 293.1450 for [M$^+$] Found: 293.1413.

EXAMPLE 10

Synthesis of Butyltoluenesulfonamide (=S5)

IUPAC: N-butyl-4-methylbenzenesulfonamide
Empirical formula: $C_{11}H_{17}NO_2S$ (MW=227.10)
Synthesis:

1.908 g of toluenesulfonic acid chloride (0.01 mol) were added in drops to 1.463 g of butylamine (0.02 mol) while stirring and heating. After cooling of the reaction mixture, 10 ml of water were added, and the reaction product was shaken out with dichloromethane (3×10 ml). The combined organic phases were washed with water (3×5 ml) and narrowed down on the rotary evaporator at reduced pressure.

Appearance: colourless oil

Yield: 2.071 g (91%) UV (MeOH) $\lambda_{max}$ nm: 226, 263 IR (KBr) $v_{max}$ cm$^{-1}$: 3290, 2960, 1600, 1330, 1160 $^1$H-NMR (500 MHz, CDCl$_3$), δ (ppm): 7.67 (2H, d, $^3J$=8.5 Hz, C-2-H und C-6-H) 7.24 (2H, d, $^3J$=8.0 Hz, C-3-H und C-5-H) 4.34 (1H, t, $^3J$=5.5 Hz, N—H) 2.87 (2H, q, $^3J$=6.5 Hz, C-1'-H) 2.36 (3H, s, C-4-Me) 1.36 (2H, m, $^3J$=8.0 Hz, C-2'-H) 1.21 (2H, m, $^3J$=8.0 Hz C-3'-H) 0.78 (3H, t, $^3J$=7.5 Hz, C-4'-H) $^{13}$C-NMR (125 MHz, CDCl$_3$), δ (ppm): 142.2 (C-4) 42.9 (C-1') 13.5 (C-4') 137.0 (C-1) 31.5 (C-2') 129.6 (C-3 und C-5) 21.5 (C-4-Me) 127.1 (C-2 und C-6) 19.6 (C-3') EI-MS (70 eV): m/z (rel. int.): 227 [M]$^+$ (42), 184 (100), 155 (90), 91 (49) High-accuracy mass determination (HR-EI-MS): Calculated: 227.0980 for [M$^+$] Found: 227.0986.

EXAMPLE 11

Synthesis of butyl-4-fluorobenzenesulfonamide (=S6)

IUPAC: N-Butyl-4-fluorobenzenesulfonamide
Empirical formula: $C_{10}H_{14}NO_2SF$ (MW=231.07)
Synthesis:

0.973 g of 4-fluorobenzenesulfonic acid chloride (0.005 mol) were added in drops to 0.732 g of butylamine (0.01 mol) while stirring and heating. After cooling of the reaction mixture, 10 ml of water were added, and the reaction product was shaken out with dichloromethane (3×10 ml). The combined organic phases were washed with water (2×5 ml) and narrowed down on the rotary evaporator at reduced pressure.

Appearance: light brown solid

Yield: 1.081 g (93%) Melting point (° C.): 33 UV (MeOH) $\lambda_{max}$ nm: 221, 260 IR (KBr) $v_{max}$ cm$^{-1}$: 1600, 1500, 1330, 1150 $^1$H-NMR (500 MHz, CDCl$_3$), δ (ppm): 7.81 (2H, dd, $^4J$ (H,F)=5.0 Hz, $^3J$ (H,H)=8.3 Hz, C-2-H and C-6-H) 7.13 (2H, t, $^3J$ (H,F)=$^3J$ (H,H)=8.3 Hz, C-3-H und C-5-H) 4.26 (1H, s, N—H) 2.89 (2H, t, $^3J$=7.5 Hz, C-1'-H) 1.36 (2H, m, $^3J$=7.5 Hz, C-2'-H) 1.22 (2H, m, $^3J$=7.5 Hz C-3'-H) 0.79 (3H, t, $^3J$=7.5 Hz, C-4'-H) $^{13}$C-NMR (125 MHz, CDCl$_3$), δ (ppm): 164.0 (C-4) 42.9 (C-1') 136.1 (C-1) 31.5 (C-2') 129.7 (C-2 und C-6) 19.7 (C-3') 116.2 (C-3 und C-5) 13.4 (C-4') EI-MS (70 eV): m/z (rel. int.): 231 [M]$^+$ (20), 188 (100), 159 (86), 95 (44) High-accuracy mass determination (HR-EI-MS): Calculated: 231.0729 for [M$^+$] Found: 231.0736.

EXAMPLE 12

Synthesis of Hydroxyethyl Benzenesulfonamide (=S7)

IUPAC: N-(2-Hydroxyethyl)benzenesulfonamide
Empirical formula: $C_8H_{11}NO_3S$ (MW=201.05)
Synthesis:

8.831 g of benzenesulfonic acid chloride (0.05 mol) and 6.720 g of ethanolamine were treated for 5 hours in 30 ml of ortho-xylene at 140° C. under reflux. After cooling, a viscous liquid settled at the bottom. This liquid was separated by a separating funnel. The viscous liquid was dissolved in 40 ml NaOH (10%). Then, the product was precipitated using concentrated hydrochloric acid and separated in the separating funnel. 50 ml of acetone were added to the product and the product was filtered (0.2 μm). Acetone was removed on the rotary evaporator under reduced pressure.

Appearance: yellowish oil

Yield: 2.739 g (27%) UV (MeOH) $\lambda_{max}$ nm: 221, 265 IR (KBr) $v_{max}$ cm$^{-1}$: 3290, 1450, 1320, 1160 $^1$H-NMR (500 MHz, CDCl$_3$), δ (ppm): 7.81 (2H, d, $^3J$=7.5 Hz, C-2-H und C-6-H) 7.51 (1H, t, $^3J$=7.5 Hz, C-4-H) 7.46 (2H, t, $^3J$=7.5 Hz, C-3-H und C-5-H) 5.26 (1H, s, N—H) 3.64 (2H, t, $^3J$=5.0 Hz, C-2'-H) 3.03 (2H, q, $^3J$=5.0 Hz, C-1'-H) 2.31 (1H, s, O—H) $^{13}$C-NMR (125 MHz, CDCl$_3$), δ (ppm): 140.6 (C-1) 59.8 (C-2') 132.2 (C-4) 45.0 (C-1') 129.0 (C-3 und C-5) 126.3 (C-2 und C-6) EI-MS (70 eV): m/z (rel. int.): 201 [M]$^+$ (4), 170 (100), 141 (84), 77 (52) High-accuracy mass determination (HR-EI-MS): Calculated: 201.0460 for [M$^+$] Found: 201.0460.

EXAMPLE 13

Synthesis of 4-fluoro-hydroxyethylbenzenesulfonamide (=S8)

IUPAC: 4-Fluoro-N-(2-hydroxyethyl)benzenesulfonamide
Empirical formula: $C_8H_{10}NO_3SF$ (MW=219.04)
Synthesis:

9.731 g 4-fluorobenzenesulfonic acid chloride (0.05 mol) and 6.720 g ethanolamine were treated under reflux for 5 hours in 30 ml ortho-xylene at 140° C. After cooling, a viscous liquid settled at the bottom, this liquid was separated by a separating funnel. The viscous liquid was dissolved in 40 ml NaOH (10%). Then the product was precipitated using concentrated hydrochloric acid and filtered off (0.7 μm). The product was washed with water (3×5 ml).

Appearance: white powder

Yield: 3.656 g (33%) Melting point (° C.): 77 UV (MeOH) $\lambda_{max}$ nm: 220, 270 IR (KBr) $v_{max}$ cm$^{-1}$: 3430, 1590, 1320, 1150 $^1$H-NMR (500 MHz, CDCl$_3$), δ (ppm): 7.81 (2H, dd, $^4$J (H,F)=5.2 Hz, $^3$J (H,H)=8.3 Hz, C-2-H und C-6-H) 7.13 (2H, t, $^3$J (H,F)=$^3$J (H,H)=8.3 Hz, C-3-H und C-5-H) 5.03 (1H, s, N—H) 3.66 (2H, t, $^3$J=6.2 Hz, C-2'-H) 3.05 (2H, t, $^3$J=4.2 Hz, C-1'-H) 1.96 (1H, s, O—H) $^{13}$C-NMR (125 MHz, CDCl$_3$), δ (ppm): 164.1 (C-4) 61.2 (C2') 135.8 (C-1) 45.1 (C-1') 129.9 (C-2 und C-6) 116.4 (C-3 und C-5) EI-MS (70 eV): m/z (rel. int.): 219 [M]$^+$ (5), 188 (100), 159 (91), 95 (56) High-accuracy mass determination (HR-EI-MS): Calculated: 219.0365 for [M$^+$] Found: 219.0367.

EXAMPLE 14

Synthesis of Pentylbenzenesulfonamide (=S9)

IUPAC: N-Pentylbenzenesulfonamide
Empirical formula: C$_{11}$H$_{17}$NO$_2$S (MW=227.10)
Synthesis:
1.766 g of benzenesulfonic acid chloride (0.01 mol) were added in drops to 1.744 g of pentylamine (0.02 mol) while stirring. After cooling of the reaction mixture, 10 ml of water were added, and the reaction product was shaken out with dichloromethane (3×10 ml). The combined organic phases were washed with water (3×5 ml) and narrowed down on the rotary evaporator at reduced pressure.
Appearance: light brown oil
Yield: 2.193 g (96%) UV (MeOH) $\lambda_{max}$ nm: 216, 264 IR (KBr) $v_{max}$ cm$^{-1}$: 3290, 2960, 2930, 1450, 1330, 1160 $^1$H-NMR (500 MHz, CDCl$_3$), δ (ppm): 7.80 (2H, d, $^3$J=7.0 Hz, C-2-H und C-6-H) 7.51 (2H, t, $^3$J=7.0 Hz, C-4-H) 7.45 (2H, t, $^3$J=7.0 Hz, C-3-H und C-5-H) 4.32 (1H, s, N—H) 2.89 (2H, q, $^3$J=7.0 Hz, C-1'-H) 1.39 (2H, m, $^3$J=6.1 Hz, C-2'-H) 1.18 (2H, m, $^3$J=3.0 Hz, C-3'-H) 1.17 (2H, m, $^3$J=3.0 Hz, C-4'-H) 0.77 (3H, t, $^3$J=7.0 Hz, C-5'-H) $^{13}$C-NMR (125 MHz, CDCl$_3$), δ (ppm): 142.1 (C-1) 44.0 (C-1') 14.2 (C-5') 133.5 (C-4) 30.3 (C2') 130.1 (C-3 und C-5) 29.8 (C-3') 127.9 (C-2 und C-6) 23.2 (C-4') EI-MS (70 eV): m/z (rel. int.): 227 [M]$^+$ (81), 170 (100), 141 (82), 77 (48) High-accuracy mass determination (HR-EI-MS): Calculated: 227.0976 for [M$^+$] Found: 227.0980.

EXAMPLE 15

Synthesis of butyl-3-trifluoromethylbenzenesulphonamide (=S10)

IUPAC: N-Butyl-3-(trifluoromethyl)benzenesulfonamide
Empirical formula: C$_{11}$H$_{14}$NO$_2$SF$_3$ (MW=281.07)
Synthesis:
978 mg of 3-trifluoromethylbenzenesulfonic acid chloride (4 mmol) were added in drops to 585 mg of butylamine (8 mmol) while stirring. After cooling of the reaction mixture, 20 ml of water were added, and the reaction product was shaken out with dichloromethane (3×10 ml). The combined organic phases were washed with water (3×5 ml) and narrowed down on the rotary evaporator at reduced pressure.
Appearance: colourless oil
Yield: 1.112 g (99%) UV (MeOH) $\lambda_{max}$ nm: 205, 220, 265 IR (KBr) $v_{max}$ cm$^{-1}$: 3290, 2960, 2940, 1610, 1330, 1160 $^1$H-NMR (500 MHz, CDCl$_3$) δ (ppm): 8.07 (1H, s, C-2-H) 7.99 (1H, d, $^3$J=7.5 Hz, C-4-H) 7.77 (1H, d, $^3$J=8.0 Hz, C-6-H) 7.62 (1H, t, $^3$J=8.0 Hz, C-5-H) 2.93 (2H, t, $^3$J=7.0 Hz, C-1'-H) 1.38 (2H, m, $^3$J=7.3 Hz C-2'-H) 1.24 (2H, m, $^3$J=7.3 Hz, C-3'-H) 0.79 (3H, t, $^3$J=7.5 Hz, C-4'-H) $^{13}$C-NMR (125 MHz, CDCl$_3$) δ (ppm): 140.4 (C-1) 128.2 (C-5) 30.5 (C2') 130.6 (q, $^2$J (C,F)=33 Hz, C-3) 123.1 (C-4) 18.7 (C-3') 129.2 (C-2) 122.1 (q, $^2$J (C,F)=220 Hz, CF$_3$) 128.9 (C-6) 42.0 (C-1') 12.5 (C-4') EI-MS (70 eV): m/z (rel. int.): 281 [M]$^+$ (8), 238 (100), 209 (84), 145 (58) High-accuracy mass determination (HR-EI-MS): Calculated: 281.0697 for [M$^+$] Found: 281.0705.

EXAMPLE 16

Synthesis of geranyl-3-trifluoromethylbenzene-sulfonamide (=S11)

IUPAC: N-[(2E)-3,7-dimethylocta-2,6-diene-1-yl]-3-(trifluoromethyl)benzenesulfonamide
Empirical formula: C$_{17}$H$_{22}$NO$_2$SF$_3$ (MW=361.13)
Synthesis:
1.233 g of 3-trifluoromethylbenzenesulfonic acid chloride (5 mmol) was dripped in 919 mg of geranylamine (6 mmol) in 40 ml of dichloromethane while stirring. After completion of the reaction, the excess amine was shaken out with hydrochloric acid (0.1 mM) (3×10 ml). Dichloromethane was removed on the rotary evaporator at reduced pressure and the product obtained.
Appearance: light brown oil
Yield: 1.770 g (98%) UV (MeOH) $\lambda_{max}$ nm: 205, 220, 265 IR (KBr) $v_{max}$ cm$^{-1}$: 3290, 2970, 2930, 1440, 1330, 1160 $^1$H-NMR (500 MHz, CDCl$_3$), δ(ppm): 8.07 (1H, s, C-2-H) 8.00 (1H, d, $^3$J=8.0 Hz, C-4-H) 7.77 (1H, d, $^3$J=8.0 Hz, C-6-H) 7.61 (1H, t, $^3$J=8.0 Hz, C-5-H) 4.95 (2H, m, $^3$J=7.0 Hz, C-2'-H und C-6'-H) 4.44 (1H, t, $^3$J=6.0 Hz, N—H) 3.57 (2H, q, $^3$J=6.5 Hz, C-1'-H) 1.89 (2H, q, $^3$J=8.0 Hz, C-5'-H) 1.83 (2H, t, $^3$J=8.0 Hz, C-4'-H) 1.59 (3H, s, C-3'-Me) 1.49 (3H, s, C-7'-Me) 1.48 (3H, s, C-8') $^{13}$C-NMR (125 MHz, CDCl$_3$) δ (ppm): 141.7 (C-3') 129.8 (C-6) 41.1 (C-1') 16.2 (C-3'-Me) 141.6 (C-1) 129.2 (C-5) 39.3 (C-4') 131.9 (C-3) 124.2 (C2') 26.1 (C-8') 131.6 (C-7') 123.5 (C-4) 25.6 (C-7'-Me) 130.3 (C-2) 118.1 (C-6') 17.6 (C-5') EI-MS (70 eV): m/z (rel. int.): 361 [M]$^+$ (39), 238 (100), 209 (67), 152 (75), 145 (58) High-accuracy mass determination: (HR-EI-MS): Calculated: 361.1323 for [M$^+$] Found: 361.1333.

EXAMPLE 17

Synthesis of Laurylbenzenesulfonamide (=S12)

IUPAC: N-Dodecylbenzenesulfonamide
Empirical formula: C$_{18}$H$_{31}$NO$_2$S (MW=325.21)
Synthesis:
177 g of benzenesulfonic acid chloride (1 mmol) were dripped in 370 mg of dodecylamine (2 mmol) in 10 ml of dichloromethane while stirring. After cooling of the reaction mixture, 10 ml of water were added, and the reaction product was shaken out with dichloromethane (3×10 ml). The combined organic phases were washed with water (3×5 ml) and narrowed down on the rotary evaporator at reduced pressure.
Appearance: colourless crystals
Yield: 323 mg (99%) Melting point (° C.): 59-61 UV (MeOH) $\lambda_{max}$ nm: 221, 265 IR (KBr) $v_{max}$ cm$^{-1}$: 3280, 2850, 1470, 1330, 1160 $^1$H-NMR (500 MHz, CDCl$_3$) δ (ppm): 7.86 (2H, d, $^3$J=8.0 Hz, C-2-H und C-6-H) 7.49 (1H, t, $^3$J 6.9 Hz, C-4-H) 7.44 (2H, t, $^3$J=8.0 Hz, C-3- H und C-5-H) 5.61 (1H, t, $^3$J=6.0 Hz, N—H) 2.86 (2H, q, $^3$J=7.0 Hz, C-1'-H) 1.39 (2H, m, $^3$J=7.1 Hz, C-2'-H) 1.19 (18H, m, C-3'-H to C-11'-H) 0.82 (3H, t, $^3$J=6.8 Hz, C-12'-H) $^{13}$C-NMR (125 MHz, CDCl$_3$) δ (ppm): 139.9 (C-1) 43.0 (C-1') 13.9 (C-12') 132.4 (C-4) 31.7 (C2') 128.7 (C-3 und C-5) 29.2 (7C, m, C-3' to C-10') 126.8

(C-2 und C-6) 22.5 (C-11') EI-MS (70 eV): m/z (rel. int.): 325 [M]$^+$ (9), 184 (88), 170 (100), 158 (58), 141 (64), 77 (21) High-accuracy mass determination (HR-EI-MS): Calculated: 325.2076 for [M$^+$] Found: 325.2080.

EXAMPLE 18

Synthesis of Butyl-4-nitro-3-trifluoromethylbenzenesulfonamide (=S13)

IUPAC: N-Butyl-4-nitro-3-(trifluoromethyl)benzenesulfonamide

Empirical formula: $C_{11}H_{13}N_2O_4SF_3$ (MW=326.05)

Synthesis:

290 mg of 4-nitro-3-trifluoromethylbenzenesulfonic acid chloride (1 mmol) in 10 ml of dichloromethane were dripped in 146 mg of butylamine (2 mmol) while stirring. After cooling of the reaction mixture, 20 ml of water were added, and the reaction product was shaken out with dichloromethane (3×10 ml). The combined organic phases were washed with water (3×5 ml) and narrowed down on the rotary evaporator at reduced pressure.

Appearance: white powder

Yield: 323 mg (99%) Melting point (° C.): 99 UV (MeOH) $\lambda_{max}$ nm: 205, 250 IR (KBr) $v_{max}$ cm$^{-1}$:3280, 2960, 1550, 1430, 1310, 1160, 1150 $^1$H-NMR (500 MHz, CDCl$_3$) δ (ppm): 8.28 (1H, s, C-2-H) 8.19 (1H, d, $^3$J=8.3 Hz, C-5-H) 7.98 (1H, d, $^3$J=8.3 Hz, C-6-H) 4.62 (1H, s, N—H) 3.03 (2H, q, $^3$J=6.3 Hz, C-1'-H) 1.49 (2H, m, $^3$J=7.3 Hz C-2'-H) 1.31 (2H, m, $^3$J=7.3 Hz, C-3'-H) 0.87 (3H, t, $^3$J=7.3 Hz, C-4'-H) $^{13}$C-NMR (125 MHz, CDCl$_3$) δ (ppm): 149.9 (C-4) 126.8 (C-5) 31.7 (C2') 144.9 (C-1) 125.0 (C-3) 19.6 (C-3') 131.8 (C-2) 123.5 (q, $^2$J (C,F)=188 Hz, CF$_3$) 126.9 (C-6) 43.2 (C-1') 13.4 (C-4') EI-MS (70 eV): m/z (rel. int.): 326 [M]$^+$ (14), 285 (22), 283 (100), 254 (82), 190 (53), 55 (17) High-accuracy mass determination (HR-EI-MS): Calculated: 326.0548 for [M$^+$] Found: 326.0553.

EXAMPLE 19

Synthesis of Geranyl-4-nitro-3-trifluoromethylbenzenesulfonamide (=S14)

IUPAC: N-[(2E)-3,7-Dimethylocta-2,6-diene-1-yl]-4-nitro-3-(trifluoromethyl)-benzenesulfonamide Empirical formula: $C_{17}H_{21}N_2O_4SF_3$ (MW=406.12)

Synthesis:

290 mg of 4-nitro-3-trifluoromethylbenzenesulfonic acid chloride (1 mmol) in 20 ml of dichloromethane were dripped in 307 mg of geranylamine (2 mmol) while stirring. After completion of the reaction, the excess amine was shaken out with hydrochloric acid (0.1 mM) (3×10 ml). Dichloromethane was removed on the rotary evaporator at reduced pressure and the product obtained.

Appearance: yellowish oil

Yield: 386 mg (95%) UV (MeOH) $\lambda_{max}$ nm: 205, 250 IR (KBr) $v_{max}$ cm$^{-1}$: 3300, 2920, 1610, 1430, 1160 $^1$H-NMR (500 MHz, CDCl$_3$) δ (ppm): 8.23 (1H, s, C-2-H) 8.14 (1H, d, $^3$J=8.5 Hz, C-5-H) 7.92 (1H, d, $^3$J=8.5 Hz, C-6-H) 4.97 (2H, m, C-2'-H und C-6'-H) 4.48 (1H, t, $^3$J=5.8 Hz, N—H) 3.63 (2H, q, $^3$J=5.8 Hz, C-1'-H) 1.88 (2H, q, $^3$J=7.5 Hz, C-5'-H) 1.85 (2H, t, $^3$J=7.5 Hz, C-4'-H) 1.61 (3H, s, C-3'-Me) 1.53 (3H, s, C-7'-Me) 1.50 (3H, s, C-8') $^{13}$C-NMR (125 MHz, CDCl$_3$), δ(ppm): 149.9 (C-4) 131.8 (C-7') 123.3 (C2') 26.1 (C-8') 145.2 (C-1) 127.0 (C-6) 117.7 (C-6') 25.6 (C-7'-Me) 142.4 (C-3') 126.9 (C-5) 41.2 (C-1') 17.6 (C-5') 132.1 (C-2) 124.7 (C-3) 39.3 (C-4') 16.2 (C-3'-Me) EI-MS (70 eV): m/z (rel. int.): 406 [M]$^+$ (77), 363 (55), 152 (96), 136 (51), 123 (100), 99 (99) High-accuracy mass determination (HR-EI-MS): Calculated: 406.1174 for [M$^+$] Found: 406.1175.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A method for treating at least one of benign prostatic hyperplasia and prostate carcinoma in a patient, comprising the steps of:

administering a medicament to a patient in need thereof, said medicament containing an isolated benzenesulfonamide derivative of the formula

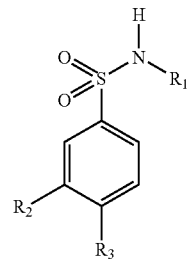

wherein $R_1$ represents an aliphatic $C_1$ to $C_{12}$ hydrocarbon or an aliphatic $C_1$ to $C_{12}$ hydrocarbon with a terminal hydroxyl group, $R_2$ is selected from the group consisting of hydrogen and a completely or partially halogenated $C_1$ residue, and $R_3$ is selected from the group consisting of hydrogen and a nitro group.

2. The method according to claim 1, wherein the prostate carcinoma is resistant to a therapy with androgen antagonists.

3. The method according to claim 2, wherein said androgen antagonists are selected from the group consisting of bicalutamide, flutamide, hydroxyflutamide, nilutamide and cyproterone acetate.

4. A method for identifying active substances that are effective in the treatment of benign prostatic hyperplasia and prostate carcinoma, said method comprising the steps of:

producing an isolated benzenesulfonamide derivative of the formula

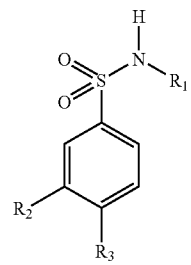

wherein $R_1$ represents an aliphatic $C_1$ to $C_{12}$ hydrocarbon or an aliphatic $C_1$ to $C_{12}$ hydrocarbon with a terminal hydroxyl group, $R_2$ is selected from the group consisting of hydrogen and a completely or partially halogenated $C_1$ residue, and $R_3$ is selected from the group consisting of hydrogen and a nitro group;

subjecting said benzenesulfonamide derivative to a test for testing anti-androgenic activity for determining the anti-androgenic effect of said benzenesulfonamide derivative; and comparing said anti-androgenic effect with the anti-androgenic effect produced by a known anti-androgenic compound in the same test.

5. The method according to claim 1, wherein said benzenesulfonamide derivative is N-butylbenzenesulfonamide.

6. The method according to claim 1, where $R_1$ is a terpenoid side chain.

7. The method according to claim 6, wherein $R_1$ is a geranyl side chain.

8. The method according to claim 6, wherein $R_1$ is selected from the group consisting of butyl and pentyl.

9. The method according to claim 1, wherein $R_2$ is trifluoromethyl.

10. The method according to claim 9, wherein $R_2$ is a geranyl side chain.

11. The method according to claim 1, wherein said benzenesulfonamide derivative is selected from the group consisting of N-methylbenzenesulfonamide, N-ethyl benzenesulfonamide, N-propylbenzenesulfonamide, N-geranylbenzenesulfonamide, N-butyl-4-methylbenzenesulfonamide, N-butyl-4-fluoro-benzenesulfonamide, N-(2-hydroxyethyl)benzenesulfonamide, 4-fluoro-N-(2-hydroxyethyl)benzenesulfonamide, N-pentyl-benzenesulfonamide, N-butyl-3-(trifluoromethyl)benzenesulfonamide, N-geranyl-3-trifluoromethyl-benzenesulfonamide, N-dodecylbenzenesulfonamide, N-butyl-4-nitro-3-trifluoromethyl-benzenesulfonamide and N-geranyl-4-nitro-3-trifluoromethyl-benzenesulfonamide.

12. The method according to claim 4, wherein said test measures the potency for inhibiting the activity of the human hormone-activated androgen receptor in a reporter gene-based test.

13. The method according to claim 12, wherein said reporter gene is a luciferase gene.

14. The method according to claim 4, wherein said test involves the use of a human prostate cancer cell whose growth is known to be androgen dependent, said method further comprising the steps of:

culturing the cells of said cell line in the presence of the compound to be tested, and determining the cell proliferation rate.

15. The method according to claim 14, wherein said cancer cell line is LNCaP.

16. The method according to claim 4, wherein said known anti-androgenic compound is β-sitosterol.

* * * * *